United States Patent
Liu et al.

(10) Patent No.: US 12,129,230 B2
(45) Date of Patent: Oct. 29, 2024

(54) DIALKYL CARBONATE PRODUCTION METHOD

(71) Applicant: MITSUBISHI GAS CHEMICAL COMPANY, INC., Tokyo (JP)

(72) Inventors: Hongyu Liu, Tokyo (JP); Takehiko Isobe, Tokyo (JP); Yousuke Shinkai, Tokyo (JP); Hidefumi Harada, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 520 days.

(21) Appl. No.: 17/297,610

(22) PCT Filed: Dec. 4, 2019

(86) PCT No.: PCT/JP2019/047310
§ 371 (c)(1),
(2) Date: May 27, 2021

(87) PCT Pub. No.: WO2020/116485
PCT Pub. Date: Jun. 11, 2020

(65) Prior Publication Data
US 2022/0009873 A1 Jan. 13, 2022

(30) Foreign Application Priority Data
Dec. 7, 2018 (JP) ................................. 2018-230256

(51) Int. Cl.
*C07C 68/04* (2006.01)
*B01J 23/10* (2006.01)

(52) U.S. Cl.
CPC ............... *C07C 68/04* (2013.01); *B01J 23/10* (2013.01)

(58) Field of Classification Search
CPC ................................. C07C 68/04; B01J 23/10
USPC ............................................................ 558/277
See application file for complete search history.

(56) References Cited

FOREIGN PATENT DOCUMENTS

| CN | 103044491 A | 4/2013 |
| CN | 108126704 A | 6/2018 |
| JP | 7-33715 A | 2/1995 |
| JP | 2012-162523 A | 8/2012 |
| JP | 2018-193354 A | 12/2018 |

OTHER PUBLICATIONS

English translation of JP 2012162523 A, published Aug. 30, 2012 (Year: 2012).*
English translation of JP 2018193354 A, published Dec. 6, 2018 (Year: 2018).*
English translation of JP H0733715 A, published Feb. 3, 1995 (Year: 1995).*
International Search Report issued in International Patent Application No. PCT/JP2019/047310, dated Mar. 3, 2020, along with English translation thereof.
Written Opinion of the International Searching Authority issued in International Patent Application No. PCT/JP2019/047310, dated Mar. 3, 2020, along with English translation thereof.
Extended European Search Report issued in corresponding European Patent Application No. 19891984.7 dated Mar. 17, 2022.
Yanning Shi et al., Research on Chemical Intermediates, 2013, 40(3), 1179-1186.
M. Aresta, et al. Journal of Organic Chemistry, 2005, 70 (16), 6177-6186.
S. Kumar et al., Journal of Materials Chemistry A, 2014, 2(44), 18861-18866.
J. Kizlink, et al., Collection of Czechoslovak Chemical Communications, 1994,59(9), 2116-2118.
J. Kizlink, et al., Collection of Czechoslovak Chemical Communications, 1995,60(4), 687-692.

* cited by examiner

*Primary Examiner* — Kristin A Vajda
(74) *Attorney, Agent, or Firm* — GREENBLUM & BERNSTEIN, P.L.C.

(57) ABSTRACT

Provided is a dialkyl carbonate production method that enables a dialkyl carbonate to be produced in a simple manner and in a short reaction time and enables easy processing of by-products. This dialkyl carbonate production method involves generation reaction of a carbonate ester through reaction between carbon dioxide and an alcohol represented by formula (1), wherein the generation reaction of a carbonate ester is performed in the presence of a carbodiimide compound represented by formula (2) ($R_1$-$R_3$ in the formula are as described in the description of the present application).

[Chemical formula 1]

$$R_1\text{—OH} \tag{1}$$

[Chemical formula 2]

$$R_2\text{—N}=\text{C}=\text{N}\text{—}R_3 \tag{2}$$

10 Claims, 2 Drawing Sheets

[Figure 1]
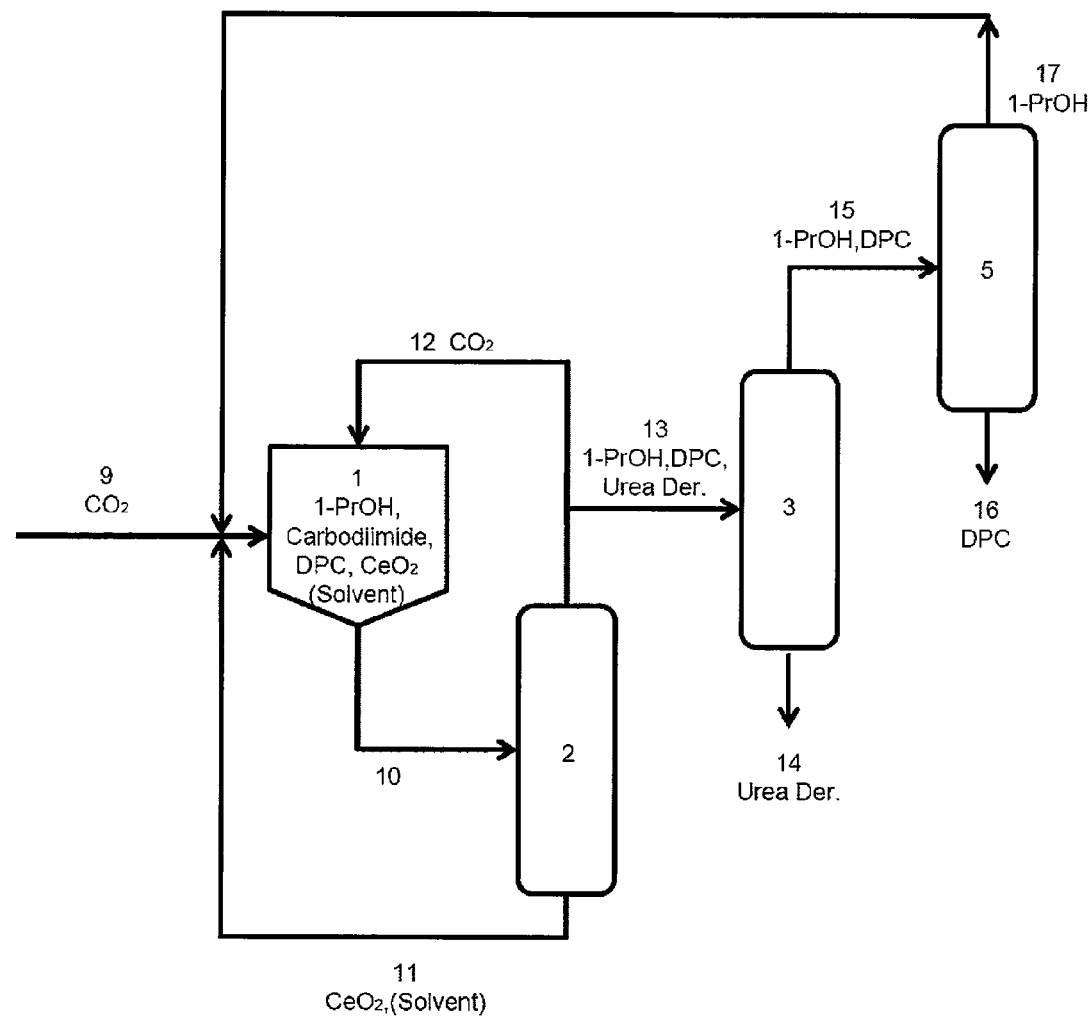

[Figure 2]
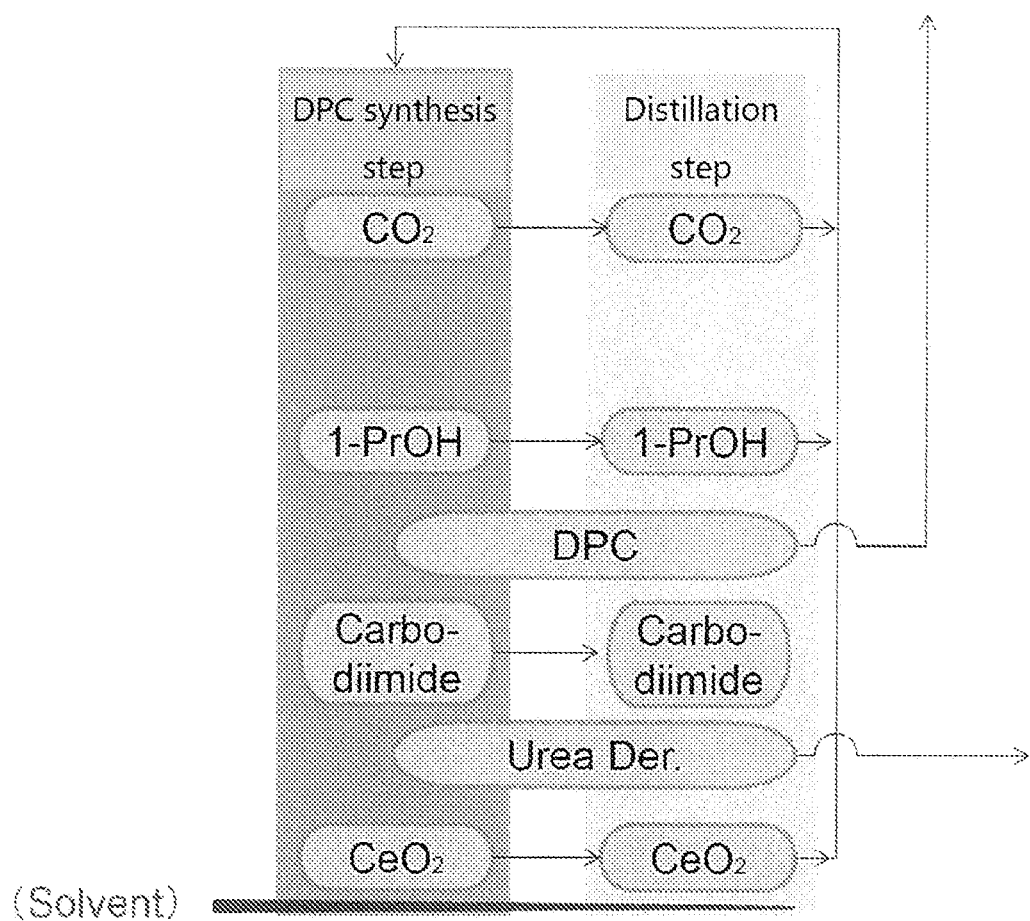

DIALKYL CARBONATE PRODUCTION METHOD

TECHNICAL FIELD

The present invention relates to a method for producing dialkyl carbonate from alcohol and carbon dioxide.

BACKGROUND ART

A dialkyl carbonate is a generic name of a compound obtained by substituting hydrogen atoms in carbonic acid, $CO(OH)_2$, with an alkyl group, and has a structure of $RO-C(=O)-OR'$ (where R and R' represent alkyl groups).

Dialkyl carbonates are very useful compounds that can be used as additives such as a gasoline additive for improving the octane number, a diesel fuel additive for reducing the amount of particles in exhaust gas, and also as an alkylation agent, a carbonylation agent, a solvent or the like that are used for synthesizing resins or organic compounds such as polycarbonate, urethane, pharmaceutical drugs, agricultural chemicals or the like, or as an electrolyte for lithium batteries, a material of a lubricant or a material of a deoxidizer for preventing rust on boiler pipes.

Direct reaction between phosgene as a source of a carbonyl and an alcohol has conventionally been the mainstream method for producing a dialkyl carbonate. Since extremely harmful and highly corrosive phosgene is used in this method, it requires great care of handling (transportation, storage, etc.) and costs to ensure maintenance and safety of the manufacturing facility. Moreover, according to this production method, a halogen such as chlorine is contained in the material or the catalyst, and thus the resulting carbonate ester contains a trace amount of halogen that cannot be removed by a simple purification process. Since the trace amount of halogen present in the carbonate ester could be a cause of corrosion that could be of a concern for application as a gasoline additive, a light oil additive or an electronic material, a thorough purification process is requisite to decrease the trace amount of halogen to an extremely minute amount. Furthermore, since this method employs phosgene which is extremely harmful to human body, recent administrative guidance has become strict such that, for example, establishment of manufacturing facilities that employ this production method is no longer authorized. Thus, a novel method for producing carbonate ester which does not use phosgene is strongly needed.

In response to this, a method for directly synthesizing a dialkyl carbonate (carbonate ester) from an alcohol and carbon dioxide by using a heterogeneous catalyst is also known. In order to increase the amount of the dialkyl carbonate generated by this method, use of 2-cyanopyridine or benzonitrile as a hydration agent has been studied to largely improve the generation amount and the generation rate of the dialkyl carbonate, to allow the reaction to easily proceed under a pressure close to a normal pressure and to increase the reaction rate (see Patent document 1).

According to the conventional methods for producing a dialkyl carbonate from an alcohol and carbon dioxide, however, the conversion rate of the alcohol used as the material and the yield of the resulting dialkyl carbonate are not high enough and there is also a problem that a relatively long time is required for the reaction.

The conventional methods for producing dialkyl carbonates also have a drawback that the by-products cannot be easily treated. For example, benzamide generated through reaction between benzonitrile and water is not always easy to remove from the reaction system, which causes a problem of increased load for the treatment for separation from benzonitrile.

PRIOR ART DOCUMENT

Patent Document

Patent document 1: Japanese Unexamined Patent Application Publication No. 2012-162523

SUMMARY OF INVENTION

Problem to be Solved by the Invention

In view of the above-described problems of the conventional techniques, the objective of the present invention is to realize a method for producing a dialkyl carbonate, by which a dialkyl carbonate can be produced in a simple manner in a short reaction time, and by which a by-product can easily be treated.

Means for Solving the Problems

In order to solve the above-described problems, the present inventors confirmed that a by-product can easily and surely be removed from the reaction system in a simple manner, and a high yield can be realized in a short reaction time by using a specific carbodiimide compound in a method for producing a carbonate ester in which the carbonate ester is directly synthesized from an alcohol and carbon dioxide. The gist of the present invention is as follows.

(I) A method for producing a dialkyl carbonate, the method comprising a carbonate ester generation reaction that involves reaction between an alcohol represented by Formula (1) below and carbon dioxide, wherein the carbonate ester generation reaction is conducted in the presence of a carbodiimide compound represented by Formula (2) below:

[Chemical formula 1]

$$R_1-OH \quad (1)$$

(wherein, $R_1$ in Formula (1) above represents an optionally branched and optionally substituted alkyl group with a carbon number of 1-10)

[Chemical formula 2]

$$R_2-NC=N-R_3 \quad (2)$$

(wherein, $R_2$ and $R_3$ in Formula (2) above are each independently selected from:
- an optionally branched alkyl group with a total carbon number of 1-20 which may be substituted with an amino group which may have one or more alkyl groups with a carbon number of 5 or less;
- an optionally branched cycloalkyl group with a carbon number of 1-20; and
- an aryl group with a total carbon number of 6-30 which may be substituted with one or more alkyl groups with a carbon number of 12 or less).

(II) The method for producing a dialkyl carbonate according to (I) above, wherein a dialkyl carbonate and water are generated and the carbodiimide compound is allowed to react with said water in the carbonate ester generation reaction.

(III) The method for producing a dialkyl carbonate according to either one of (I) and (II) above, wherein $R_2$ and $R_3$ in Formula (2) above are each independently selected from:
- an optionally branched alkyl group with a total carbon number of 1-12 which may be substituted with an amino group which may have one or more alkyl groups with a carbon number of 3 or less;
- an optionally branched cycloalkyl group with a carbon number of 1-12; and
- an aryl group with a total carbon number of 6-20 which may be substituted with one or more alkyl groups with a carbon number of 10 or less.

(IV) The method for producing a dialkyl carbonate according to any one of (I)-(III) above, wherein the carbodiimide compound is represented by Formula (2-1) below:

[Chemical formula 3]

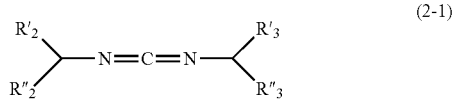
(2-1)

(wherein, $R'_2$, $R''_2$, $R'_3$ and $R''_3$ in Formula (2-1) above are each independently selected from hydrogen, and an optionally branched alkyl group with a carbon number of 6 or less which may be substituted with an amino group which may have an alkyl group with a carbon number of 3 or less, or $R'_2$ and $R''_2$ are attached to each other to form an optionally branched cycloalkyl group with a carbon number of 5-10, or $R'_3$ and $R''_3$ are attached to each other to form an optionally branched cycloalkyl group with a carbon number of 5-10).

(V) The method for producing a dialkyl carbonate according to any one of (I)-(III) above, wherein $R_2$ and $R_3$ in Formula (2) above are identical.

(VI) The method for producing a dialkyl carbonate according to any one of (I)-(III) above, wherein at least one of $R_2$ and $R_3$ in Formula (2) above is an isopropyl group.

(VII) The method for producing a dialkyl carbonate according to any one of (I)-(VI) above, wherein the amount of the carbodiimide compound added is 0.1-1.0 mole relative to 1.0 mole of the alcohol.

(VIII) The method for producing a dialkyl carbonate according to any one of (I)-(VII) above, wherein the carbonate ester generation reaction is conducted in the presence of a solid catalyst and the solid catalyst contains cerium oxide.

(IX) The method for producing a dialkyl carbonate according to any one of (I)-(VIII) above, wherein the carbonate ester generation reaction is conducted in the presence of an inorganic catalyst.

(X) The method for producing a dialkyl carbonate according to any one of (I)-(IX) above, wherein no solvent is used in the carbonate ester generation reaction.

(XI) The method for producing a dialkyl carbonate according to any one of (I)-(X) above, wherein the reaction temperature of the carbonate ester generation reaction is 100° C. or higher but lower than 200° C.

(XII) The method for producing a dialkyl carbonate according to any one of (I)-(XI) above, wherein the reaction pressure of the carbonate ester generation reaction is 1 MPa or higher but 20 MPa or lower.

Advantageous Effect of Invention

According to the present invention in which a carbonate ester generation reaction that involves reaction between an alcohol and carbon dioxide is allowed to take place in the presence of a specific carbodiimide compound as described above, a method for producing a dialkyl carbonate can be realized, by which the dialkyl carbonate can be produced in a simple manner and in short reaction time and a by-product can be easily treated.

BRIEF DESCRIPTION OF DRAWINGS

FIG. 1 One example of a device for producing a dialkyl carbonate.

FIG. 2 A chart showing the state of each substance in each step in the production device shown in FIG. 1.

EMBODIMENTS FOR CARRYING OUT THE INVENTION

Hereinafter, a preferred embodiment of the present invention will be described in detail. The present invention should not be limited to the following embodiment, and can be altered and carried out in any way within the scope that has the effect of the invention.

<1. Method for Producing Dialkyl Carbonate>

The method for producing a dialkyl carbonate according to the present invention comprises a carbonate ester generation reaction that involves reaction between an alcohol and carbon dioxide.

As shown in the chemical formula below, reaction between an alcohol and carbon dioxide in the carbonate ester generation reaction generates water along with a carbonate ester such as a dialkyl carbonate, and hydration reaction between the generated water and a carbodiimide compound present in the reaction system generates an urea derivative. Accordingly, although a dialkyl carbonate and water are generated by the carbonate ester generation reaction, the generated water can be removed from or reduced in the reaction system via the reaction between water and the carbodiimide compound. By efficiently removing water from the reaction system, generation of the dialkyl carbonate can be promoted.

Moreover, since the urea derivative, i.e., by-product, precipitates as a solid, it can be easily removed from the liquid reaction system.

[Chemical formula 4]

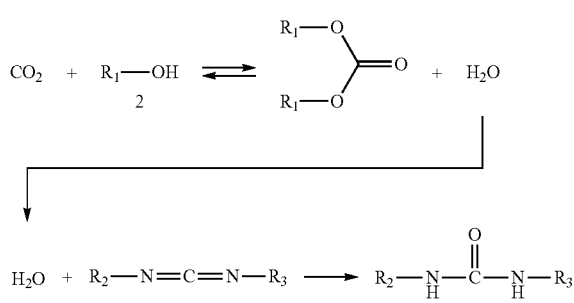

<2. Substrates of Carbonate Ester Generation Reaction>

In the carbonate ester generation reaction, specific kinds of alcohol and carbodiimide compound are used as will be described below.

(Alcohol)

An alcohol used in the carbonate ester generation reaction is an alcohol represented by Formula (1) below.

[Chemical formula 5]

$R_1$—OH       (1)

In Formula (1), $R_1$ is an optionally branched and optionally substituted alkyl group with a carbon number of 1-10. The carbon number of $R_1$ is preferably 1-6 and more preferably 1-3.

In the carbonate ester generation reaction, any alcohol selected from one or more kinds of primary alcohols, secondary alcohols and tertiary alcohols can also be used.

Examples of such alcohol include methanol, ethanol, 1-propanol, isopropanol, 1-butanol, 1-pentanol, 1-hexanol, 1-heptanol, 1-octanol, 1-nonanol, allyl alcohol, 2-methyl-1-propanol, cyclohexanemethanol, benzyl alcohol, ethylene glycol, 1,2-propanediol and 1,3-propanediol. Use of such alcohols is favorable since they increase the yield of the product and improve the reaction rate. Carbonate esters generated with the above-mentioned alcohols are dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonane carbonate, diaryl carbonate, di-2-methyl-propyl carbonate, dicyclohexanemethyl carbonate, dibenzyl carbonate, ethylene carbonate, 1,2-propylene carbonate and 1,3-propylene carbonate, respectively.

When the resulting carbonate ester is used as a material of diaryl carbonate, the alcohol is preferably an alcohol with a carbon number of 1-6 and more preferably an alcohol with a carbon number of 2-4.

Moreover, a monohydric or a dihydric alcohol is preferably used.

(Carbon Dioxide)

Carbon dioxide in the carbonate ester generation reaction may not only be one prepared as industrial gas but also be one separated and collected from exhaust gas from factories or ironworks that are producing products, power plant or the like.

(Carbodiimide Compound)

A compound represented by Formula (2) below is used as the carbodiimide compound used in the carbonate ester generation reaction.

[Chemical formula 6]

(2)

$R_2$ and $R_3$ in Formula (2) are each independently selected from:
(a) an optionally branched alkyl group with a total carbon number of 1-20 which may be substituted with an amino group which may have one or more alkyl groups with a carbon number of 5 or less;
(b) an optionally branched cycloalkyl group with a carbon number of 1-20; or
(c) an aryl group with a total carbon number of 6-30 which may be substituted with one or more alkyl groups with a carbon number of 12 or less.

$R_2$ and $R_3$ may be (a') an optionally branched alkyl group with a total carbon number of 1-12 which may be substituted with an amino group which may have one or more alkyl groups with a carbon number of 3 or less. In this case, the amino group has, for example, a methyl group. Moreover, the total carbon number of the alkyl group is preferably 2-8 and more preferably 3-6.

$R_2$ and $R_3$ may alternatively be (b') an optionally branched cycloalkyl group with a carbon number of 1-12. In this case, the carbon number of the cycloalkyl group is preferably 2-10 and more preferably 3-8.

In addition, $R_2$ and $R_3$ may alternatively be (c') an aryl group with a total carbon number of 6-20 which may be substituted with one or more alkyl groups with a carbon number of 10 or less. In this case, the alkyl group is, for example, an alkyl group with a carbon number of 1-6 such as an isopropyl group. Moreover, the total carbon number of the aryl group is preferably 8-16. For example, the aryl group may be a dialkylphenyl group.

$R_2$ and $R_3$ in Formula (2) above may be identical. Moreover, at least one of $R_2$ and $R_3$ in Formula (2) may be an isopropyl group.

In the carbonate ester generation reaction, a compound represented by Formula (2-1) below is favorably used.

[Chemical formula 7]

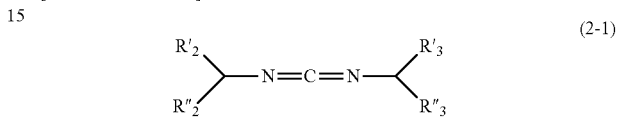

(2-1)

In Formula (2-1), $R'_2$, $R''_2$, $R'_3$ and $R''_3$ may each independently be selected from hydrogen, and an optionally branched alkyl group with a carbon number of 6 or less which may be substituted with an amino group which may have an alkyl group with a carbon number of 3 or less. In this case, the above-described amino group is, for example, a dimethylamino group, while the alkyl group with a carbon number of 6 or less may be, for example, an ethyl group, a propyl group or the like.

Furthermore, $R'_2$ and $R''_2$ may be attached to each other or $R'_3$ and $R''_3$ may be attached to each other to form an optionally branched cycloalkyl group with a carbon number of 5-10, for example, a cyclohexyl group.

Specific examples of the preferable carbodiimide compound include dicyclohexylcarbodiimide, diisopropylcarbodiimide, 1-ethyl-3-(3-dimethylaminopropyl)carbodiimide and bis(2,6-diisopropylphenyl)carbodiimide.

In the carbonate ester generation reaction, an urea derivative is generated from the carbodiimide compound and water, and this urea derivative precipitates as a solid. Therefore, water can easily and efficiently be removed from the reaction system as a part of the urea derivative. Hence, the reaction rate of the reaction that gives a dialkyl carbonate from the alcohol and carbon dioxide can be improved. Now, the carbodiimide compound may be regenerated from the urea derivative to be recycled.

<3. Components in Carbonate Ester Generation Reaction Other than Reaction Substrate>

(Catalyst)

A catalyst can be used to promote the carbonate ester generation reaction. In the carbonate ester generation reaction, a solid catalyst is preferably used. Although the solid catalyst preferably contains cerium oxide as follows, a catalyst containing other component can also be used. For example, the catalyst contains either one or both of $CeO_2$ and $ZrO_2$. Examples of such catalyst include $CeO_2$ alone, $ZrO_2$ alone, a mixture of $CeO_2$ and $ZrO_2$, and a solid solution or a composite oxide of $CeO_2$ and $ZrO_2$, among which a catalyst of $CeO_2$ alone is particularly preferable. In the case of a solid solution or a composite oxide of $CeO_2$ and $ZrO_2$, the mixture ratio of $CeO_2$ and $ZrO_2$ is basically 50:50 but it may be changed suitably.

Moreover, the catalyst used in the carbonate ester generation reaction is preferably an inorganic catalyst, for example, a catalyst containing either one of $CeO_2$ or $ZrO_2$ mentioned above, rather than an organic metal catalyst. This is because, for example, an organic metal catalyst containing an alkoxy group, an alkyl group or the like cannot be produced easily and is also inferior to an inorganic catalyst in terms of the reaction efficiency.

The above-described catalyst may be in a form of either powder or a molded product, where such molded product may have any shape like a sphere shape, pellets, a cylindrical shape, a ring shape, a wheel shape, granules or the like.

(Solvent)

Since the alcohol and the carbodiimide compound as the reaction substrates in the carbonate ester generation reaction are usually highly compatible, reaction can proceed without a solvent. Without the need of a solvent, the reaction device of the carbonate ester generation reaction can be simplified and a dialkyl carbonate can be generated efficiently from fewer kinds of materials.

In the carbonate ester generation reaction, however, a solvent, for example, an aromatic hydrocarbon-based solvent such as benzene, alkylbenzene, dialkylbenzene, naphthalene, alkylnaphthalene or diphenylbenzene may be used.

<4. Conditions for Carbonate Ester Generation Reaction>

(Ratio of Reaction Substrates)

For the carbonate ester generation reaction, the amount of the carbodiimide compound added is preferably 0.1-1.0 mole relative to 1.0 mole of the alcohol. The amount of the carbodiimide compound added is more preferably 0.2-0.8 moles and still more preferably 0.4-0.6 moles relative to 1.0 mole of the alcohol.

While the amount of carbon dioxide used relative to the amount of the alcohol is not particularly limited, a saturated solution where carbon dioxide is dissolved in the alcohol to the (maximum) solubility that is defined according to the kind of the alcohol, the temperature and the reaction pressure can be used for the carbonate ester generation reaction.

(Reaction Temperature)

The reaction temperature of the carbonate ester generation reaction is preferably 100° C. or higher but lower than 200° C. The reaction temperature is more preferably 110° C. or higher but lower than 180° C. and still more preferably 120° C. or higher but lower than 150° C.

(Reaction Pressure)

The reaction pressure of the carbonate ester generation reaction is preferably 1 MPa or higher but 20 MPa or lower. The reaction pressure is more preferably 1.5 MPa or higher but 10 MPa or lower and still more preferably 2 MPa or higher but 8 MPa or lower.

(Reaction Time)

While the reaction time of the carbonate ester generation reaction is suitably adjusted according to the targeted yield and the like, it is, for example, within 10 hours, preferably within 6 hours and more preferably within 4 hours. According to the present invention, the carbonate ester generation reaction can proceed rapidly and a dialkyl carbonate can be generated at high yield in the above-mentioned reaction time.

<5. Device for Producing Carbonate Ester>

Hereinafter, a specific example will be described to illustrate a production device used for the present invention in more detail. FIG. 1 shows one example of a preferable facility. In addition, FIG. 2 is a chart schematically showing the state of each substance in each step in the facility shown in FIG. 1.

A solid catalyst (solid phase) of either one or both of $CeO_2$ and $ZrO_2$, an alcohol (1-propanol (1-PrOH); liquid phase), a carbodiimide compound (liquid phase) and carbon dioxide ($CO_2$ (9); gas phase) supplied via a boost blower (not shown) are fed into a carbonate ester reactor 1 (first reaction part).

The solid catalyst can be newly fed prior to the reaction or a solid catalyst collected from the catalyst separating column 2 can be used.

In the device used for the present invention that directly synthesizes a carbonate ester, a solid catalyst of either one or both of $CeO_2$ and $ZrO_2$ is used, and any of a batch reactor, a semi-batch reactor, a continuous reactor, or a flow reactor such as a tubular reactor can be used as the synthesizer.

The temperature of the reaction solution in the carbonate ester reactor 1 is preferably set to 100-200° C. If the temperature of the reaction solution is lower than 100° C., the reaction rate tends to be low, which will delay the progress of the carbonate ester generation reaction and deteriorate the carbonate ester productivity. On the other hand, if the temperature of the reaction solution exceeds 200° C., the reaction rate of each reaction will be high but there is a risk of causing degradation or degeneration of the carbonate ester. Since, however, the ideal temperature of the reaction solution is considered to vary depending on the kind and the amount of the solid catalyst and the amount and the ratio of the material (alcohol), it is favorable to determine the optimal conditions accordingly. In addition, since the preferable temperature of the reaction solution is 100-150° C., the material (alcohol) is preferably pre-heated with steam or the like before entering the carbonate ester reactor.

The reaction pressure in the carbonate ester reactor 1 is preferably set to 1-20 MPa (absolute pressure). If the reaction pressure is less than 1 MPa (absolute pressure), a decompression device will be required, which not only complicates the facility and increases the cost but also requires power energy for decompression and thus has a risk of deteriorating the energy efficiency. On the other hand, if the reaction pressure exceeds 20 MPa, hydration reaction with 2-cyanopyridine or the like becomes hard to proceed, which not only deteriorates the yield of the carbonate ester but also requires power energy for boosting and thus has a risk of deteriorating the energy efficiency. In addition, from the viewpoint of increasing the yield of the carbonate ester, the reaction pressure is more preferably 1.5-10 MPa (absolute pressure) and still more preferably 2-8 MPa (absolute pressure).

The carbodiimide compound used for the hydration reaction is preferably introduced into the reactor prior to the reaction in an amount of moles that is 0.1 times or more but 1.0 time of less the theoretical amount of moles of water that is by-produced via the reaction between the materials, i.e., alcohol and $CO_2$. More preferably, the carbodiimide compound is used in an amount of moles that is 0.2 times or more but 0.8 times or less and particularly preferably 0.4 times or more but 0.6 times or less the theoretical amount of moles of water that is by-produced via the reaction between the materials, i.e., alcohol and C02. By adjusting the amount of the carbodiimide compound used as described above, the yield of the dialkyl carbonate can be improved and the side reaction can be suppressed.

The reaction product can be separated by distillation separation. Specifically, a reaction solution 10 resulting from the reaction in the carbonate ester reactor 1 is sent to the catalyst separating column 2, where the catalyst is collected from the bottom of the catalyst separating column 2 while $CO_2$ (12), 1-PrOH, dipropyl carbonate (DPC) and the like (13) are collected from the top of the column. The collected catalyst and $CO_2$ are recycled in the carbonate ester reactor 1.

The mixture (13) collected from the catalyst separating column 2 is sent to the by-product separating column 3, where an urea derivative resulting from water and the carbodiimide compound (14: Urea Der.) is collected from the bottom of the by-product separating column 3 while 1-PrOH and DPC (15) are collected from the top of the column.

1-PrOH and DPC (15) collected from the top of the by-product separating column 3 are sent to the carbonate ester collecting column 5, where DPC (16) is collected from the bottom of the carbonate ester collecting column while 1-PrOH (17) is collected from the top of the column. The collected 1-PrOH is recycled in the carbonate ester reactor 1.

As described above, in the carbonate ester generation reaction, the by-products can be easily removed by solid-liquid separation, while the reaction product and the compound to be recycled can be separated only by distillation separation. By employing such carbonate ester generation reaction of the present invention, a dialkyl carbonate can be produced efficiently in a few production steps and the device can be simplified.

EXAMPLES

Hereinafter, the present invention will be described in more detail by means of examples, although the present invention should not be limited to these examples.

Example 1

2.8 mmol of cerium oxide ($CeO_2$) was sintered at 600° C. in air atmosphere for 3 hours to obtain a powdery solid catalyst.

Subsequently, 0.48 g (2.8 mmol) of the above-described solid catalyst, 140 mmol of N,N'-diisopropylcarbodiimide (available from Tokyo Chemical Industry Co., Ltd.) as the dehydrating agent and 280 mmol of 1-propanol (available from Wako Pure Chemical Corporation) were fed into an autoclave (with two inclined stirring paddles, material SUS316, volume 200 mL). Following replacement with $CO_2$, 27 g (613 mmol) of $CO_2$ was introduced into the autoclave to give a reaction pressure of 8 MPa. Thereafter, the temperature was increased while stirring the reaction system. The time point when the temperature reached 132° C. was considered to be the start of the reaction.

Following reaction at 132° C. for 4 hours, the autoclave was water-cooled to 25° C. and then depressurized, to which 1-hexanol was added as an internal standard. The product was collected to analyze the yield of dipropyl carbonate (DPrC) by GC. As a result, 14.4 g (98.4 mmol) of dipropyl carbonate (DPrC) was generated.

Conditions for quantitating the yield of dipropyl carbonate (DPrC) by gas chromatography (GC) were as follows.

Method used for measurement: GC-FID method

Device used for measurement: Shimadzu GC-2014 available from Shimadzu Corporation Internal standard: 1-Hexanol Examples 2-13

Dialkyl carbonates such as DPrC were obtained in the same manner as Example 1 except that the kind of the dehydrating agent, the amount of the solid catalyst, the kind and the amount of the alcohol and the reaction pressure were varied as indicated in Table 1. The results are shown in Table 1.

TABLE 1

| | Materials | | | | | Reaction conditions | | | Reaction results | | |
|---|---|---|---|---|---|---|---|---|---|---|---|
| | Kind of dehydrating agent | Dehydrating agent (mmol) | $CeO_2$ (mmol) | Kind of alcohol | Alcohol (mmol) | $CO_2$ (mmol) | Temperature (° C.) | Pressure (MPa) | Time (hr) | Kind of dialkyl carbonate | Yield of dialkyl carbonate (mmol) | Yield of dialkyl carbona (mol %) |
| Example 1 | N,N'-Diisopropyl-carbodiimide | 140 | 2.8 | 1-Propanol | 280 | 613 | 132 | 8 | 4 | DPrC | 98.4 (14.4 g) | 70.3 |
| Example 2 | N,N'-Dicyclohexyl-carbodiimide | 140 | 2.8 | 1-Propanol | 280 | 613 | 132 | 8 | 4 | DPrC | 91.1 (13.3 g) | 65.02 |
| Example 3 | 1-(3-Dimethyl-aminopropyl)-3-ethylcarbodiimide | 140 | 2.8 | 1-Propanol | 280 | 613 | 132 | 8 | 4 | DPrC | 49.5 (7.2 g) | 35.38 |
| Example 4 | Bis(2,6-diisopropylphenyl)carbodiimide | 140 | 2.8 | 1-Propanol | 280 | 613 | 132 | 8 | 4 | DPrC | 0.5 (0.08 g) | 0.37 |
| Example 5 | N,N'-Di-tert-butylcarbodiimide | 140 | 2.8 | 1-Propanol | 280 | 613 | 132 | 8 | 4 | DPrC | 8.1 (1.2 g) | 5.75 |
| Example 6 | N,N'-Diisopropyl-carbodiimide | 140 | 2.8 | Methanol | 280 | 613 | 132 | 8 | 4 | DMC | 108.9 (9.8 g) | 77.8 |
| Example 7 | N,N'-Diisopropyl-carbodiimide | 140 | 2.8 | Ethanol | 280 | 613 | 132 | 8 | 4 | DEC | 100.3 (11.9 g) | 71.66 |
| Example 8 | N,N'-Diisopropyl-carbodiimide | 140 | 2.8 | N-Butanol | 280 | 613 | 132 | 8 | 4 | DBC | 90.6 (15.8 g) | 64.68 |
| Example 9 | N,N'-Diisopropyl-carbodiimide | 140 | 1.4 | 1-Propanol | 840 | 153 | 132 | 2 | 4 | DPrC | 68.6 (10.0 g) | 48.98 |
| Example 10 | N,N'-Dicyclohexyl-carbodiimide | 140 | 1.4 | 1-Propanol | 840 | 153 | 132 | 2 | 4 | DPrC | 58.1 (8.5 g) | 41.51 |
| Example 11 | 1-(3-Dimethyl-aminopropyl)-3-ethylcarbodiimide | 140 | 1.4 | 1-Propanol | 840 | 153 | 132 | 2 | 4 | DPrC | 46.7 (6.8 g) | 33.37 |
| Example 12 | Bis(2,6-diisopropylphenyl)carbodiimide | 140 | 1.4 | 1-Propanol | 840 | 153 | 132 | 2 | 4 | DPrC | 0.9 (0.13 g) | 0.66 |
| Example 13 | N,N'-Di-tert-butylcarbodiimide | 140 | 1.4 | 1-Propanol | 840 | 153 | 132 | 2 | 4 | DPrC | 3.3 (0.48 g) | 2.36 |

Comparative Example 1

Reaction was carried out in the same manner as Example 1 except that no dehydrating agent was used, and the amount of the catalyst, the kind of the alcohol, the amount of the alcohol used, and the like were changed. As a result, 0.016 g (0.09 mmol) of DBC (dibutyl carbonate (di-n-butyl carbonate)) was generated as shown in Table 2 below.

(Comparative examples 2-12) Attempts were made to produce dialkyl carbonates such as DMC (dimethyl carbonate) in the same manner as Comparative example 1 except that the reaction conditions were varied as indicated in Table 2 below. The results are shown in Table 2.

Reference Example 1

Reaction was carried out in the same manner as Example 1 except that 140 mmol of benzonitrile was used as the dehydrating agent, and the amount of the catalyst was changed. As a result, 0.088 g (0.60 mmol) of DPrC was generated as shown in Table 2 below.

Reference Examples 2-5

Attempts were made to produce dialkyl carbonates such as DPrC in the same manner as Reference example 1 except that the reaction conditions were varied as indicated in Table 2 below. The results are shown in Table 2.

While preferred embodiments of the present invention have been described in detail with reference to the attached drawings, the present invention is not limited to these embodiments. A person having ordinary skill in the art to which the present invention pertains would obviously conceive of various alterations and modifications within the scope of the technical ideas defined by the claims, and such alterations and modifications should be construed as being duly within the technical scope of the present invention.

DESCRIPTION OF REFERENCE NUMERALS

1 Carbonate ester reactor
2 Catalyst separating column
3 By-product separating column
5 Carbonate ester collecting column

The invention claimed is:

1. A method for producing a dialkyl carbonate, the method comprising a carbonate ester generation reaction that involves reaction between an alcohol represented by Formula (1) below and carbon dioxide, wherein the carbonate ester generation reaction is conducted in the presence of a carbodiimide compound represented by Formula (2) below, and
   wherein the amount of the carbodiimide compound is 0.4-0.6 mole relative to 1.0 mole of the alcohol:

$$R_1-OH \qquad (1)$$

TABLE 2

| | Materials | | | | | Reaction conditions | | | Reaction results | | |
|---|---|---|---|---|---|---|---|---|---|---|---|
| | Kind of dehydrating agent | Dehydrating agent (mmol) | $CeO_2$ (mmol) | Kind of alcohol | Alcohol (mmol) | $CO_2$ (mmol) | Temperature (°C.) | Pressure (MPa) | Time (hr) | Kind of dialkyl carbonate | Yield of dialkyl carbonate (mmol) | Yield of dialkyl carbona (mol %) |
| Comparative example 1 | No dehydrating agent | 0 | 1 | N-Butanol | 100 | 613 | 132 | 8 | 16 | DBC | 0.09 (0.016 g) | 0.19 |
| Comparative example 2 | 2-Methoxy-benzonitrile | 50 | 1 | N-Butanol | 100 | 613 | 132 | 8 | 16 | DBC | 0.11 (0.019 g) | 0.22 |
| Comparative example 3 | 2-Methoxy-phenylacetonitrile | 50 | 1 | N-Butanol | 100 | 613 | 132 | 8 | 16 | DBC | 0.11 (0.019 g) | 0.23 |
| Comparative example 4 | 2-Nitro-benzonitrile | 140 | 1.4 | 1-Propanol | 840 | 613 | 132 | 8 | 3 | DPrC | 0.13 (0.019 g) | 0.09 |
| Comparative example 5 | N,N'-Diisopropyl-carbodiimide | 140 | 2.8 | Phenol | 280 | 613 | 132 | 8 | 4 | DPhC | 0.00 (0.0 g) | 0 |
| Comparative example 6 | No dehydrating agent | 0 | 0.06 | Methanol | 200 | 613 | 132 | 8 | 2 | DMC | 0.05 (0.005 g) | 0.05 |
| Comparative example 7 | Silica gel | 17 (1 g) | 0.06 | Methanol | 200 | 613 | 132 | 8 | 2 | DMC | 0.00 (0.0 g) | 0 |
| Comparative example 8 | Molecular sieve 4A | 1 g | 0.06 | Methanol | 200 | 613 | 132 | 8 | 2 | DMC | 0.01 (0.001 g) | 0.01 |
| Comparative example 9 | CaO | 18 (1 g) | 0.06 | Methanol | 200 | 613 | 132 | 8 | 2 | DMC | 0.01 (0.001 g) | 0.07 |
| Comparative example 10 | $CaCl_2$ | 9 (1 g) | 0.06 | Methanol | 200 | 613 | 132 | 8 | 2 | DMC | 0.01 (0.001 g) | 0.08 |
| Comparative example 11 | $Mg_2SO_4$ | 8 (1 g) | 0.06 | Methanol | 200 | 613 | 132 | 8 | 2 | DMC | 0.02 (0.002 g) | 0.21 |
| Comparative example 12 | $Na_2SO_4$ | 7 (1 g) | 0.06 | Methanol | 200 | 613 | 132 | 8 | 2 | DMC | 0.00 (0.0 g) | 0 |
| Reference example 1 | Benzonitrile | 140 | 35 | 1-Propanol | 280 | 613 | 132 | 8 | 4 | DPrC | 0.60 (0.088 g) | 0.44 |
| Reference example 2 | Benzonitrile | 50 | 1 | N-Butanol | 100 | 613 | 132 | 8 | 16 | DBC | 0.25 (0.044 g) | 0.5 |
| Reference example 3 | 2-Furonitrile | 140 | 1.4 | 1-Propanol | 840 | 613 | 132 | 8 | 3 | DPrC | 5.41 (0.791 g) | 3.8 |
| Reference example 4 | Aminobenzonitrile | 140 | 1.4 | 1-Propanol | 840 | 613 | 132 | 8 | 3 | DPrC | 2.21 (0.323 g) | 1.6 |
| Reference example 5 | 2-Dimethylamino-acetonitrile | 140 | 1.4 | 1-Propanol | 840 | 613 | 132 | 8 | 3 | DPrC | 0.63 (0.092 g) | 0.45 | wherein $R_1$ in Formula (1) above represents an optionally branched and optionally substituted alkyl group with a carbon number of 1-10

 (2)

wherein $R_2$ and $R_3$ in Formula (2) above are each independently selected from:

an optionally branched alkyl group with a total carbon number of 1-20 which may be substituted with an amino group which may have one or more alkyl groups with a carbon number of 5 or less;

an optionally branched cycloalkyl group with a carbon number of 1-20; and an aryl group with a total carbon number of 6-30 which may be substituted with one or more alkyl groups with a carbon number of 12 or less; and wherein a dialkyl carbonate and water are generated and the carbodiimide compound is allowed to react with said water in the carbonate ester generation reaction.

2. The method for producing the dialkyl carbonate according to claim 1, wherein $R_2$ and $R_3$ in Formula (2) above are each independently selected from:

an optionally branched alkyl group with a total carbon number of 1-12 which may be substituted with an amino group which may have one or more alkyl groups with a carbon number of 3 or less;

an optionally branched cycloalkyl group with a carbon number of 1-12; and an aryl group with a total carbon number of 6-20 which may be substituted with one or more alkyl groups with a carbon number of 10 or less.

3. The method for producing the dialkyl carbonate according to claim 1, wherein the carbodiimide compound is represented by Formula (2-1) below:

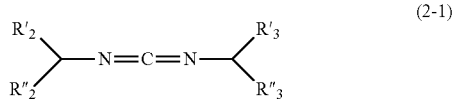 (2-1)

wherein $R'_2$, $R''_2$, $R'_3$ and $R''_3$ in Formula (2-1) above are each independently selected from hydrogen, and an optionally branched alkyl group with a carbon number of 6 or less which may be substituted with an amino group which may have an alkyl group with a carbon number of 3 or less, or $R'_2$ and $R''_2$ are attached to each other to form an optionally branched cycloalkyl group with a carbon number of 5-10, or $R'_3$ and $R''_3$ are attached to each other to form an optionally branched cycloalkyl group with a carbon number of 5-10.

4. The method for producing the dialkyl carbonate according to claim 1, wherein $R_2$ and $R_3$ in Formula (2) above are identical.

5. The method for producing the dialkyl carbonate according to claim 1, wherein at least one of $R_2$ and $R_3$ in Formula (2) above is an isopropyl group.

6. The method for producing the dialkyl carbonate according to claim 1, wherein the carbonate ester generation reaction is conducted in the presence of a solid catalyst and the solid catalyst contains cerium oxide.

7. The method for producing the dialkyl carbonate according to claim 1, wherein the carbonate ester generation reaction is conducted in the presence of an inorganic catalyst.

8. The method for producing the dialkyl carbonate according to claim 1, wherein no solvent is used in the carbonate ester generation reaction.

9. The method for producing the dialkyl carbonate according to claim 1, wherein the reaction temperature of the carbonate ester generation reaction is 100° C. or higher but lower than 200° C.

10. The method for producing the dialkyl carbonate according to claim 1, wherein the reaction pressure of the carbonate ester generation reaction is 1 MPa or higher but 20 MPa or lower.

* * * * *